US009994513B2

(12) United States Patent
Hayakawa et al.

(10) Patent No.: US 9,994,513 B2
(45) Date of Patent: Jun. 12, 2018

(54) METHOD FOR PRODUCING NOVEL ALI CYCLIC ESTER COMPOUND, NOVEL ALICYCLIC ESTER COMPOUND, (METH)ACRYLIC COPOLYMER PRODUCED BY POLYMERIZING SAID COMPOUND, AND PHOTOSENSITIVE RESIN COMPOSITION USING SAID COPOLYMER

(71) Applicant: Mitsubishi Gas Chemical Company, Inc., Tokyo (JP)

(72) Inventors: Shoichi Hayakawa, Mie (JP); Hiroshi Horikoshi, Tokyo (JP); Kikuo Furukawa, Tokyo (JP); Hiroyasu Tanaka, Tokyo (JP); Hiroyuki Tanagi, Tokyo (JP)

(73) Assignee: Mitsubishi Gas Chemical, Inc., Tokyo (JP)

( * ) Notice: Subject to any disclaimer, the term of this patent is extended or adjusted under 35 U.S.C. 154(b) by 0 days. days.

(21) Appl. No.: 15/117,668

(22) PCT Filed: Feb. 12, 2015

(86) PCT No.: PCT/JP2015/053865
§ 371 (c)(1),
(2) Date: Aug. 9, 2016

(87) PCT Pub. No.: WO2015/122470
PCT Pub. Date: Aug. 20, 2015

(65) Prior Publication Data
US 2016/0355461 A1 Dec. 8, 2016

(30) Foreign Application Priority Data

Feb. 14, 2014 (JP) .................................. 2014-026749

(51) Int. Cl.
C07C 231/12 (2006.01)
C07C 231/02 (2006.01)
C07C 235/40 (2006.01)
C08F 220/18 (2006.01)
G03F 7/039 (2006.01)
H01L 21/027 (2006.01)
C08F 20/36 (2006.01)

(52) U.S. Cl.
CPC .......... *C07C 231/12* (2013.01); *C07C 231/02* (2013.01); *C07C 235/40* (2013.01); *C08F 20/36* (2013.01); *C08F 220/18* (2013.01); *G03F 7/039* (2013.01); *G03F 7/0392* (2013.01); *G03F 7/0397* (2013.01); *C07C 2603/74* (2017.05); *C08F 2220/1808* (2013.01); *C08F 2800/20* (2013.01)

(58) Field of Classification Search
CPC ... C07C 231/12; C07C 235/40; C07C 231/02; C08F 220/18; C08F 20/36; C08F 2800/20; C08F 2220/108; G03F 7/039; G03F 7/0397

See application file for complete search history.

(56) References Cited

U.S. PATENT DOCUMENTS

| 6,656,659 | B1 | 12/2003 | Nozaki et al. | |
|---|---|---|---|---|
| 2003/0180662 | A1* | 9/2003 | Nakano | G03F 7/039 430/270.1 |
| 2004/0058270 | A1* | 3/2004 | Iwai | G03F 7/0397 430/270.1 |
| 2005/0266351 | A1* | 12/2005 | Takemoto | C07C 69/73 430/311 |
| 2012/0196228 | A1* | 8/2012 | Nagasawa | G03F 7/0045 430/285.1 |

FOREIGN PATENT DOCUMENTS

| JP | H04-039665 A | 2/1992 |
|---|---|---|
| JP | H10-319595 A | 12/1998 |
| JP | 2000-026446 A | 1/2000 |
| JP | 2003-167346 A | 6/2003 |
| JP | 2004-323704 A | 11/2004 |
| JP | 2005-331918 A | 12/2005 |
| JP | 2006-243474 A | 9/2006 |
| JP | 2008-129388 A | 6/2008 |

(Continued)

OTHER PUBLICATIONS

English translation of JP, 2011-227463, A (2011) from machine translation from AIPN Japan Patent Office National Center for Industrial Property Information and Training, generated Jan. 10, 2017, 45 pages.*
English translation of JP, 2011-123143, A (2011) from machine translation from AIPN Japan Patent Office National Center for Industrial Property Information and Training, generated Jan. 10, 2017, 50 pages.*
March, Jerry, Advanced Organic Chemistry : REactions, Mechanisms, and Structure, 0-56 on pp. 384-385 , year 1977, second edition, printed in Untied States, GcGraw Hill series in Advanced Chemistry.*
English translation of JP, 2011-37953, A (2011) from machine translation from AIPN Japan Patent Office National Center for Industrial Property Information and Training, generated Jun. 24, 2017, 21 pages.*
English translation of JP, 2012-118518, A (2012) from machine translation from AIPN Japan Patent Office National Center for Industrial Property Information and Training, generated Jan. 10, 2017, 121 pages.*

(Continued)

*Primary Examiner* — Cynthia Hamilton
(74) *Attorney, Agent, or Firm* — Fitch, Even, Tabin & Flannery LLP

(57) ABSTRACT

Provided are a resist and a compound for the resist improving the sensitivity, the resolution and the line edge roughness (LER) in a good balance without spoiling basic properties of a chemical amplification resist such as pattern shape, dry etching resistance, heat resistance and the like. Provided are a method for producing an alicyclic ester compound expressed by general formula (1), an alicyclic ester compound expressed by general formula (1), a (meth)acrylic copolymer obtained by polymerization of the alicyclic ester compound, and a photosensitive resin composition containing the (meth)acrylic copolymer. A method for producing an alicyclic ester compound expressed by general formula (1) includes reacting an adamantane compound expressed by general formula (2) with hydroxyalkylamine expressed by general formula (3) to produce an adamantaneamide compound expressed by general formula (4), and then reacting the adamantaneamide compound expressed by general formula (4) with (meth)acrylic acid.

13 Claims, No Drawings

(56) References Cited

FOREIGN PATENT DOCUMENTS

| JP | 2009-258598 A | 11/2009 |
|---|---|---|
| JP | 2010-270333 A | 12/2010 |
| JP | 2011-037953 A | 2/2011 |
| JP | 2011-123143 A | 6/2011 |
| JP | 2011-227463 A | 11/2011 |
| JP | 2012-118518 A | 6/2012 |
| JP | 2012-168502 A | 9/2012 |
| TW | 2012-02842 A | 1/2012 |
| WO | 2011/034007 A1 | 3/2011 |
| WO | 2012/008546 A1 | 1/2012 |

OTHER PUBLICATIONS

Hsieh et al Jouarnal of Polymer Science: Part A: Polymer Chemistry, vol. 26, pp. 2501-2515 (1988).*

Maruyama, Ken et al., "EUV resist development for 16nm half pitch." SPIE Advanced Lithography, Mar. 29, 2012, p. 83250A-83250A, International Society for Optics and Photonics.

Kozawa, Takahiro et al. "Modeling and simulation of acid diffusion in chemically amplified resists with polymer-bound acid generator." Applied Physics Express, Jul. 4, 2012, p. 074301, vol. 5, Issue 7.

Jikken Kagaku Kota 16, 5th Edition (2007), pp. 119-126.

Development of Oil-Refining Chemical Industry (2009) vol. 10, pp. 21-24.

International Search Report dated May 19, 2015 for PCT/JP2015/053865 and English translation of the same (5 pages).

Office Action issued on the corresponding Chinese Patent Application No. 201580007729.4 dated Jul. 4, 2017; English translation submitted herewith (16 pages).

Zhou Nianchen Li Xin, Organic Chemistry, 2nd Edition, Soochow University Press, Oct. 2012, p. 225, and English Translation (5 pages).

* cited by examiner

METHOD FOR PRODUCING NOVEL ALICYCLIC ESTER COMPOUND, NOVEL ALICYCLIC ESTER COMPOUND, (METH)ACRYLIC COPOLYMER PRODUCED BY POLYMERIZING SAID COMPOUND, AND PHOTOSENSITIVE RESIN COMPOSITION USING SAID COPOLYMER

CROSS-REFERENCE TO RELATED APPLICATIONS

This application is a U.S. national phase application filed under 35 U.S.C. § 371 of International Application PCT/JP2015/053865, filed on Feb. 12, 2015, designating the United States, which claims priority from Japanese Application Number 2014-026749, filed Feb. 14, 2014.

FIELD OF THE INVENTION

The present invention relates to a novel alicyclic ester compound, a (meth)acrylic copolymer and a photosensitive resin composition containing the same that are usable as an optical material of, for example, a resist for a KrF, ArF or F2 excimer laser, or a chemical amplification resist for an X-ray, an electron beam, or EUV (extreme ultraviolet) light, usable as a material of a resin composition having superb heat resistance, chemical resistance and light transmittance, and usable as a material of any of various other industrial resin compositions.

BACKGROUND OF THE INVENTION

Semiconductor devices are strongly desired to be further reduced in size as flash memories as storage devices now have a larger capacity and markets of, for example, image sensors for high resolution cameras of mobile phones and smartphones are expanded. For producing various electronic devices, photolithography is widely used. Photolithography has contributed to the size reduction of semiconductor devices by using light sources of light having a shorter wavelength. In the case where a KrF excimer laser or any other laser that emits light of a shorter wavelength is used as a light source, a chemical amplification resist is generally used. A commonly used chemical amplification resist is a solution containing a functional resin as a main component, a photoacid generator, and several types of additives. It is important that the functional resin as the main component should have characteristics such as etching resistance, adherence to a substrate, transparency to light from the light source to be used, development rate and the like in a good balance. Such characteristics of the functional resin determine the resist performance.

The functional resin used for a photoresist for a KrF excimer laser is generally a polymer containing a vinyl compound, an acrylate or the like as a repeat unit. A functional resin proposed for a resist for KrF excimer laser lithography is a hydroxystyrene-based resin (Patent Document 1). A functional resin proposed for a resist for ArF excimer laser lithography is an acrylic resin containing an adamantyl(meth)acrylate as a basic backbone (Patent Documents 2 through 6). The basic backbone of the functional resin is now being defined. However, a functional resin is not used in the state of containing a single repeat unit. A reason for this is that a resin containing a single repeat unit does not fulfill all the necessary characteristics including the etching resistance and the like. In actuality, a functional resin is formed of a copolymer containing a plurality of, namely, two or more, repeat units including functional groups each for improving a characteristic, and the functional resin is combined with a photoacid generator or the like and dissolved in a solvent to form a photosensitive resin composition to be used.

Recently, size reduction is advanced with the lithography process. ArF excimer laser lithography is advanced and now uses liquid immersion exposure and even double patterning exposure. In addition, lithography using extreme ultraviolet (EUV) light, which is a target of attention as a next-generation lithography technology, and electron beam direct drawing, have been developed in various manners.

Although various developments have been made for the purpose of further size reduction, the influence of contrast deterioration caused by diffusion of acid that is generated from a photoacid generator after the exposure has become more serious as the width of the circuit is decreased. Methods for controlling the acid diffusion now proposed include a method of enlarging the structure of the photoacid generator (Non-patent Document 1) and a method of using a resin containing a monomer that contains a photoacid generator (Patent Document 7, Non-patent Document 2). Another method now proposed is a method of extending a pendant part of a resist polymer to block an acid diffusion path (Patent Documents 8 and 9).

With the double patterning exposure technology, an LLE (litho-litho-etch) process is now being studied. According to the LLE process, a first pattern is formed of a first resist material, then a pattern is formed of a second resist material while the first resist pattern is maintained, and the two patterns are subjected to dry etching at the same time. In this process, the patterns are made insoluble by a crosslinking reaction that is caused by heating. If the glass transition temperature of the first resist material is low, a flow of the pattern is generated, which is not preferable.

In such a situation, Patent Documents 11 and 12 propose a photoresist polymer having an amide bond and an adamantane structure but provide no example in which such a photoresist polymer is actually produced. It has not been known whether such a photoresist polymer is actually usable.

PRIOR ART DOCUMENTS

Patent Documents

Patent Document 1: JP 2006-243474
Patent Document 2: JP Hei 4-39665
Patent Document 3: JP Hei 10-319595
Patent Document 4: JP 2000-26446
Patent Document 5: JP 2003-167346
Patent Document 6: JP 2004-323704
Patent Document 7: JP 2012-168502
Patent Document 8: JP 2005-331918
Patent Document 9: JP 2008-129388
Patent Document 10: JP 2011-123143
Patent Document 11: WO2011/34007
Patent Document 12: WO2012/8546

Non-Patent Documents

Non-patent Document 1: SPIE, 8325-10 (2012)
Non-patent Document 2: SPIE, 8322-05 (2012)

SUMMARY OF THE INVENTION

For the above-described reasons, it is strongly desired to develop a photosensitive resin composition that improves the sensitivity, the resolution and the line edge roughness with no adverse influence on the basic characteristics of the photosensitive resin composition, has a high glass transition temperature, and has superb rectangularity.

The present invention has an object of providing a compound usable for a chemical amplification resist, sensitive to a KrF excimer laser, an ArF excimer laser, an F2 excimer laser, an electron beam and EUV light, the compound solving the above-described problems and being compatible to size reduction of a semiconductor substrate circuit that is further advanced in the future, and also providing a method for producing such a compound.

As a result of active studies made to solve the above-described problems, the present inventors found that a novel alicyclic ester compound having a long chain structure expressed by general formula (1) and also including an adamantane structure that includes an amide bond and a hydroxyl group, and a photosensitive resin composition including this alicyclic ester compound as a repeat unit, have a good sensitivity, improve various resist performances such as the resolution, the line edge roughness and the like, have a high glass transition temperature, and are superb in rectangularity in a lithography operation performed by use of a KrF excimer laser, an ArF excimer laser, an F2 excimer laser, an X-ray, an electron beam or EUV (extreme ultraviolet) light, and thus are useful and expected to solve the various problems caused by the size reduction of semiconductor circuits. Thus, the present invention has been achieved. The present invention also relates to a method for producing the above-described novel alicyclic ester compound. According to this method, the novel alicyclic ester compound is produced at high yield.

More specifically, the present invention is as follows.

(I) A method for producing an alicyclic ester compound expressed by general formula (1):

[Chemical formula 1]

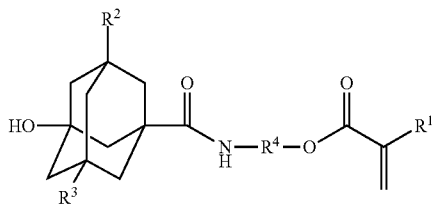

(1)

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5;

the method comprising reacting an adamantane compound expressed by general formula (2) with hydroxyalkylamine expressed by general formula (3) to produce an adamantaneamide compound expressed by general formula (4), and then reacting the adamantaneamide compound expressed by general formula (4) with (meth)acrylic acid:

[Chemical formula 2]

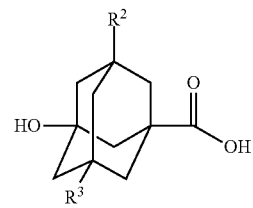

(2)

where $R^2$ and $R^3$ are the same as those in chemical formula (1);

[Chemical Formula 3]

$H_2N-R^4-OH$ (3)

where $R^4$ is the same as that in chemical formula (1);

[Chemical formula 4]

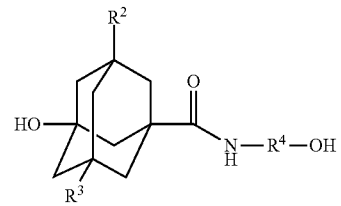

(4)

where $R^2$, $R^3$ and $R^4$ are the same as those in chemical formula (1).

(II) The method for producing an alicyclic ester compound according to (I) above, the method further comprising the step of heating the adamantane compound expressed by general formula (2) and the hydroxyalkylamine expressed by general formula (3) to cause dehydration condensation to produce the adamantaneamide compound expressed by general formula (4) as shown below:

[Chemical formula 5]

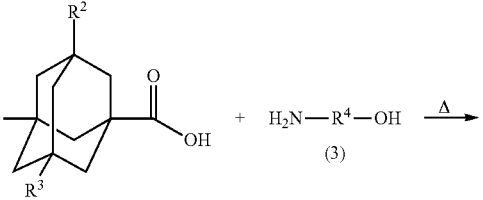

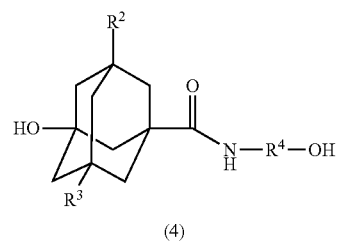

(III) A method for producing an alicyclic ester compound expressed by general formula (1):

[Chemical formula 6]

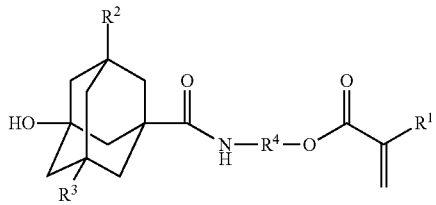

(1)

where R¹ represents a hydrogen atom or a methyl group, R² and R³ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and R⁴ represents a linear or branched alkylene group having a carbon number of 2 to 5;

the method comprising reacting an adamantane compound expressed by general formula (2) with aminoalkyl (meth)acrylate expressed by general formula (5) to produce the alicyclic ester compound expressed by general formula (1):

[Chemical formula 7]

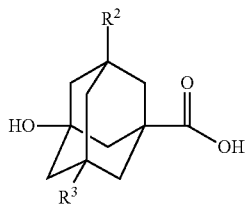

(2)

where R² and R³ are the same as those in chemical formula (1);

[Chemical formula 8]

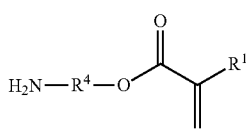

(5)

where R¹ and R⁴ are the same as those in chemical formula (1).

(IV) The method for producing an alicyclic ester compound according to (III) above, wherein the reaction, expressed by the following formula, of the adamantane compound expressed by general formula (2) and the aminoalkyl (meth)acrylate expressed by general formula (5) uses a dehydration condensation agent:

[Chemical formula 9]

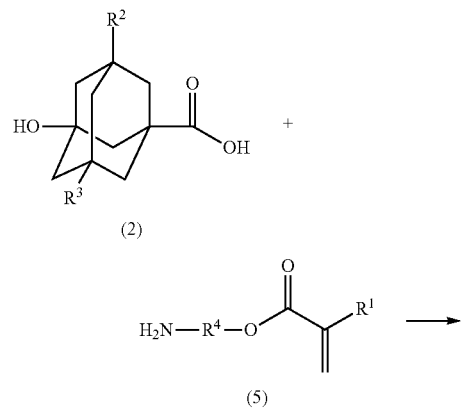

(V) A (meth)acrylic copolymer, comprising a repeat unit expressed by general formula (6), the (meth)acrylic copolymer being obtained by polymerization of the alicyclic ester compound produced by the method according to any one of (I) through (IV):

[Chemical formula 10]

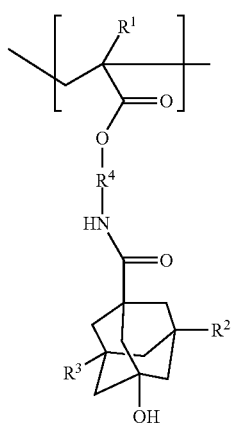

(6)

where R¹ through R⁴ are the same as those in general formula (1).

(VI) The (meth)acrylic copolymer according to (V) above, further comprising at least one type of repeat unit expressed by general formula (7) or (8) and at least one type of repeat unit expressed by general formula (9) or (10):

[Chemical formula 11]

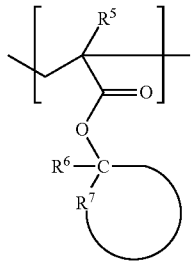

(7)

where $R^5$ represents hydrogen or a methyl group, $R^6$ represents an alkyl group having a carbon number of 1 to 4, and $R^7$ represents a cycloalkylene group having a carbon number of 5 to 20, or an alicyclic alkylene group;

[Chemical formula 12]

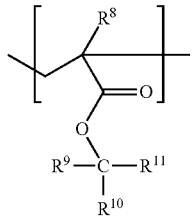

(8)

where $R^8$ represents hydrogen or a methyl group, $R^9$ and $R^{10}$ may be the same as, or different from, each other and independently represent an alkyl group having a carbon number of 1 to 4, and $R^{11}$ represents an alkyl group having a carbon number of 1 to 4, a cycloalkyl group having a carbon number of 5 to 20, or an alicyclic alkyl group;

Chemical formula 13]

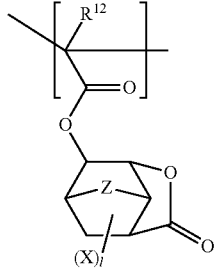

(9)

where $R^{12}$ represents hydrogen or a methyl group, Z represents methylene(-CH$_2$—) or oxa(-O—), X(s) may be the same as, or different from, each other and independently represent a hydroxyl group, a halogen group, a nitrile group, a carboxylic acid group, an alkyl carboxylate group having a carbon number of 1 to 4, or an alkoxide group having a carbon number of 1 to 4, and I represents 0 to 2;

[Chemical formula 14]

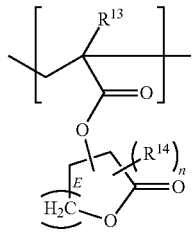

(10)

where $R^{13}$ represents hydrogen or a methyl group, m represents 1 to 3, $R^{14}$ represents a methyl group, an ethyl group, a hydroxyl group or a halogen group, and n represents 0 to 2.

(VII) A photosensitive resin composition, comprising the (meth)acrylic copolymer according to (V) or (VI) above and a photoacid generator.

(VIII) An alicyclic ester compound expressed by general formula (1):

[Chemical formula 15]

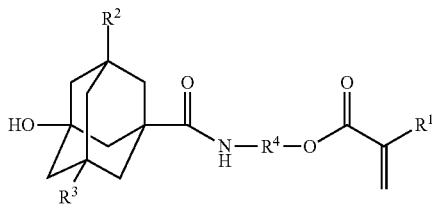

(1)

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5.

An alicyclic ester compound according to the present invention is preferable as a material of various resin compositions such as various functional polymers and the like used because of the heat resistance, surface hardness, and chemical resistance thereof, and especially improves the resolution and the line edge roughness when being used as a component of a copolymer of a chemical amplification resist for a KrF excimer laser, an ArF excimer laser, an F2 excimer laser, an X-ray, an electron beam or EUV (extreme ultraviolet) light.

DESCRIPTION OF EMBODIMENTS

Hereinafter, the present invention will be described in more detail. An alicyclic ester compound including an adamantane structure that includes an amide bond and a hydroxyl group is expressed by general formula (1).

The alicyclic ester compound according to the present invention that is expressed by general formula (1) is obtained by reacting an adamantane compound expressed by general formula (2) with hydroxyalkylamine expressed by general formula (3) to produce an adamantaneamide compound expressed by general formula (4), and then reacting the adamantaneamide compound expressed by general formula (4) with (meth)acrylic acid (production method 1). Alternatively, the alicyclic ester compound according to the present invention that is expressed by general formula (1) is obtained by reacting the adamantane compound expressed by general formula (2) with aminoalkyl (meth)acrylate expressed by general formula (5) (production method 2).

[Chemical formula 16]

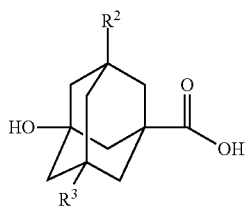

(2)

(In the formula, $R^2$ and $R^3$ are the same as those in chemical formula (1).)

[Chemical Formula 17]

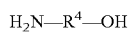

(3)

(In the formula, $R^4$ is the same as that in chemical formula (1).)

[Chemical formula 18]

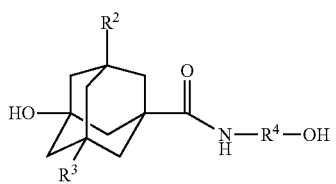

(4)

(In the formula, $R^2$, $R^3$ and $R^4$ are the same as those in chemical formula (1).)

[Chemical formula 19]

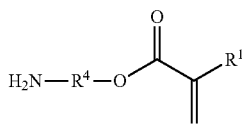

(5)

(In the formula, $R^1$ and $R^4$ are the same as those in chemical formula (1).)

Specifically, the alicyclic ester compound expressed by general formula (1) may be, for example, as follows.

[Chemical formula 20]

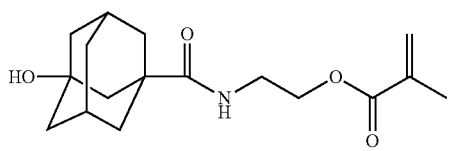

-continued

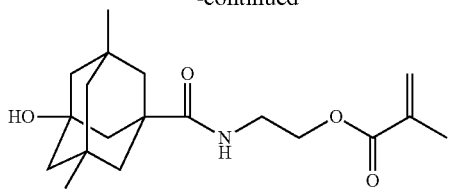

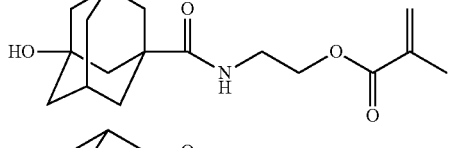

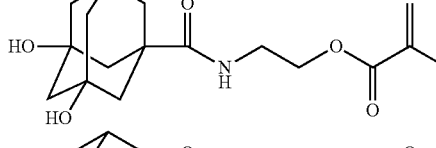

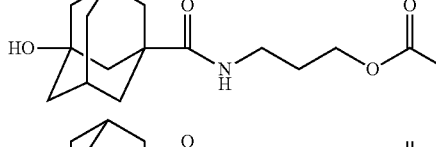

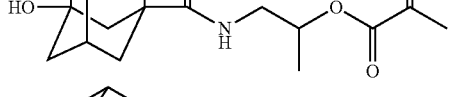

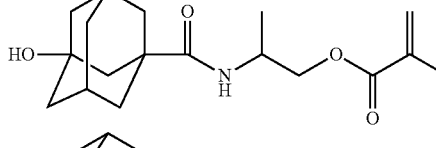

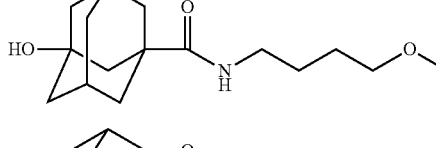

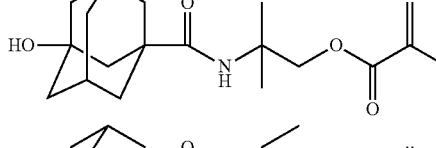

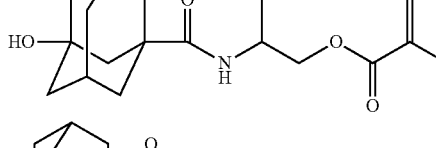

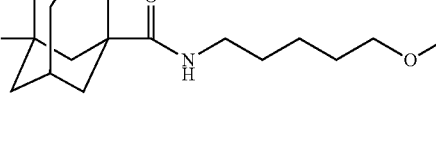

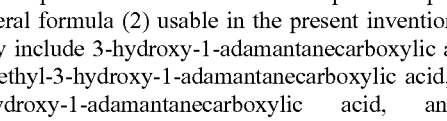

Examples of the adamantane compound expressed by general formula (2) usable in the present invention specifically include 3-hydroxy-1-adamantanecarboxylic acid, 5,7-dimethyl-3-hydroxy-1-adamantanecarboxylic acid, 5-ethyl-3-hydroxy-1-adamantanecarboxylic acid, and 3,5-dihydroxy-1-adamantanecarboxylic acid.

Specifically, the hydroxyalkylamine expressed by general formula (3) usable in the present invention may be, for example, as follows.

[Chemical formula 21]

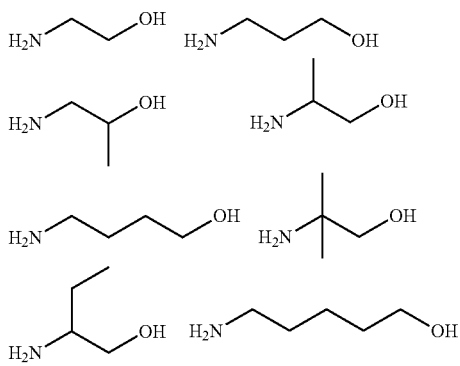

Specifically, the aminoalkyl (meth)acrylate expressed by general formula (5) usable in the present invention may be, for example, as follows:

[Chemical formula 22]

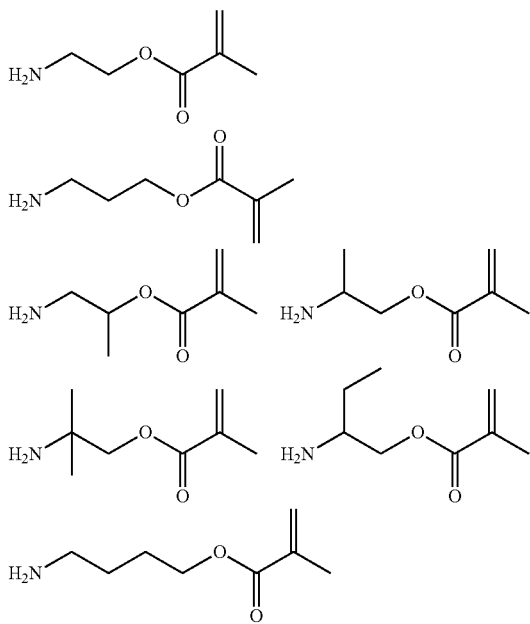

and salts thereof.

The alicyclic ester compound of general formula (1) includes a part having a low polarity with certainty because $R^4$ is an alkylene group having a relatively long chain with a carbon number of 2 to 5. Therefore, the alicyclic ester compound of general formula (1) prevents the above-described diffusion of acid generated from a photoacid generator. For these reasons, a photosensitive resin compound containing the alicyclic ester compound of general formula (1) realizes selective exposure of only a necessary region, and thus has a low limiting resolution and a high sensitivity.

It is preferable that at least one of $R^2$ and $R^3$ of general formula (1) is not a hydroxyl group. An alicyclic ester compound as a monol in which neither $R^2$ nor $R^3$ is a hydroxyl group or as a diol in which either $R^2$ or $R^3$ is a hydroxyl group has an appropriate polarity. Therefore, a photosensitive resin composition containing a (meth)acrylic copolymer that contains such an alicyclic ester compound is recognized to have the following effects. A photosensitive resin composition containing a (meth)acrylic copolymer having an appropriate polarity suppresses the water solubility of a part not exposed by an alkali development step to be significantly lower than that of an exposed part, and thus prevents the resist film loss and the dissolution of a pattern. A (meth)acrylic copolymer having an appropriate polarity also has a superb solubility in representative resist solvents, for example, propyleneglycol monomethylether acetate (PGMEA) and propyleneglycol monomethyl ether (PGME), cyclohexane.

An alicyclic ester compound as the above-described monol or diol is usually available more easily than, for example, a triol. In addition, a reaction of generating an adamantane compound as a monol or a diol (see chemical formula (2) below) easily introduces a single carboxyl group selectively into the adamantane backbone.

<Production Method 1>

Production method 1 will be described. Production method 1 corresponds to (I) and (II) above of the present invention. For reacting an adamantane compound expressed by general formula (2) with hydroxyalkylamine expressed by general formula (3) to produce an adamantaneamide compound expressed by general formula (4), use of a dehydration condensation method by heating is desirable. Use of an acid halogenation method is not preferable because a hydroxyl group of the adamantane compound expressed by general formula (2) as a material is halogenated. Use of a reaction with a dehydration condensation agent such as N,N'-dicyclohexylcarbodiimide or the like is not preferable because the target substance is not obtained. The hydroxyalkylamine of general formula (3) is incorporated, with respect to the adamantane compound of general formula (2), at 0.3 to 20.0 equivalent, preferably at 0.5 to 10.0 equivalent, or more preferably at 0.8 to 5.0 equivalent. With such a range of amount of the hydroxyalkylamine, the reaction progresses sufficiently. When the amount of the hydroxyalkylamine is too large, it is difficult to remove an excessive amount of the hydroxyalkylamine, which is not preferable.

The reaction of the adamantane compound of general formula (2) and the hydroxyalkylamine of general formula (3) is an equilibrium reaction. Therefore, water generated during the reaction needs to be removed from the system, which requires a distillation device to be provided in a reactor. This reaction needs to be performed at a high temperature. Specific reaction conditions are to be appropriately set in accordance with the concentration of the matrix or the catalyst to be used. General conditions are as follows. The reaction temperature is 130° C. to 250° C., preferably 140° C. to 220° C., or more preferably 150° C. to 200° C. The reaction time duration is 1 hour to 30 hours, preferably 2 hours to 20 hours, or more preferably 3 hours to 10 hours. The pressure may be normal pressure, reduced pressure or increased pressure. The reaction process may be appropriately selected from known processes such as a batch process, a semi-batch process, a continuous process and the like.

According to the present invention, the reaction of the adamantane compound expressed by general formula (2) and the hydroxyalkylamine expressed by general formula (3) may be performed by use of a solvent. Specific examples of the usable solvent include diethyleneglycol diethylether, diethyleneglycol dibutylether, 1,2-dibutoxyethane, nitrobenzene, dimethylsulfoxide, and sulfolane. The reaction may be performed with no solvent.

The reaction of the adamantaneamide compound expressed by general formula (4) and (meth)acrylic acid to produce the alicyclic ester compound expressed by general formula (1), a known esterification method is usable such as, for example, an acid anhydride method using (meth)acrylic acid anhydride, an acid halogen method using (meth)acrylic acid chloride or the like, or an esterification method using a dehydration condensation agent, for example, a dehydration condensation agent described below in <Production method 2>. In order to improve the selectivity with the hydroxyl group bonded to the adamantyl group, the acid anhydride method or the esterification method using a dehydration condensation agent is desirable.

<Production Method 2>

Production method 2 will be described. Production method 2 corresponds to (III) and (IV) above of the present invention. For reacting an adamantane compound expressed by general formula (2) with aminoalkyl (meth)acrylate expressed by general formula (5) to produce the alicyclic ester compound expressed by general formula (1), use of a dehydration condensation agent is simple and preferable. Specific examples of the usable dehydration condensation agent include carbodiimide-based dehydration condensation agents such as N,N'-dicyclohexylcarbodiimide, N,N'-diisopropylcarbodiimide, 1-ethyl-3-(3-dimethylaminopropyl) carbodiimidehydrochloride and the like; mixed acid anhydride-derived dehydration condensation agents such as 2,4,6-trichlorobenzoylchloride, 2-methyl-6-nitrobenzoic anhydride, 2,4,6-trichlorobenzoylchloride, and the like; and active ester-derived dehydration condensation agents such as bis(pentafluorophenyl) carbonate and the like. The dehydration condensation agent is incorporated, with respect to the adamantane compound, at 1.0 to 10.0 equivalent, preferably at 1.1 to 5.0 equivalent, or more preferably at 1.3 to 3.0 equivalent. With such a range of amount of the dehydration condensation agent, the reaction progresses sufficiently, and there is no need to remove an excessive amount of the dehydration condensation agent, which is preferable. Alternatively, an esterification condensation catalyst is preferably usable. A specific example of the esterification condensation catalyst is dimesitylammoniumpentafluorobenzenesulfonate. The dehydration condensation agent is incorporated, with respect to the adamantane compound, preferably at 0.001 to 0.1 equivalent, or more preferably at 0.005 to 0.5 equivalent. With such a range of amount of the dehydration condensation agent, the reaction progresses sufficiently, which is economically preferable.

In the case where a carbodiimide-based dehydration condensation agent is used, it is preferable to also use a promotor. Specific examples of the usable promotor are those that are known as being usable with a carbodiimide-based dehydration condensation agent in a dehydration condensation reaction, namely, pyridine, 4-dimethylaminopyridine, 1-hydroxybenzotriazole, 1-hydroxy-7-azabenzotriazole, N-hydroxysuccinimide, N-hydroxy-5-norbornene-2,3-dicarboxylate imide, and 4-nitrophenol. The promotor is incorporated, with respect to the adamantane compound, preferably at 0.001 to 0.1 equivalent, or more preferably at 0.005 to 0.05 equivalent. With such a range of amount of the promotor, the reaction progresses sufficiently, which is economically preferable.

In the case where a salt of aminoalkyl (meth)acrylate expressed by general formula (5) is used for the reaction, it is preferable to also use a basic compound that neutralizes the salt. Specific examples of the usable basic compound include trimethylamine, triethylamine, tripropylamine, diisopropylethylamine, tributylamine, tripentylamine, trihexylamine, N,N-dimethylaniline, phenyldimethylamine, diphenylmethylamine, triphenylamine, 1,8-diazabicyclo[5.4.0]-7-undecene, 1,5-diazabicyclo[4.3.0]-5-nonene, pyridine, 2-methylpyridine, 3-methylpyridine, 4-methylpyridine, 2,6-dimethylpyridine, and 4-dimethylaminopyridine. The basic compound is incorporated, with respect to the salt of aminoalkyl (meth)acrylate, at 0.5 to 3 equivalent, preferably at 0.7 to 2 equivalent, or more preferably at 0.9 to 1.5 equivalent.

According to the present invention, the reaction of the adamantane compound expressed by general formula (2) and the aminoalkyl (meth)acrylate expressed by general formula (5) to produce the alicyclic ester compound expressed by general formula (1) may be performed by use of a solvent. Specific examples of the usable solvent include dimethylsulfoxide, diethylether, diisopropylether, tetrahydrofuran, dioxane, dimethylacetamide, dimethylformamide, acetonitrile, benzene, toluene, chloroform, chlorobenzene, dichloroethane, dichloromethane, acetone, methyl ethyl ketone, and methyl isobutyl ketone. The solvent to be used varies in accordance with the dehydration condensation agent to be used. In the case where a carbodiimide-based dehydration condensation agent is used, it is preferable to use a solvent having a low dielectric constant. As is known, in the case where a carbodiimide-based dehydration condensation agent is used, it is important to suppress a side reaction thereof that results in the formation of acyl urea. For this purpose, it is important to select an appropriate solvent. A chlorine-based solvent such as chloroform, dichloroethane, dichloromethane or the like suppresses a rearrangement reaction that results in the formation of acyl urea, which is a side reaction, and thus is preferably usable. The solvent is incorporated at 1 to 100 parts by mass, or preferably at 3 to 10 parts by mass, with respect to 1 part by mass of adamantane compound expressed by general formula (2). Acyl urea is generated by a one-molecule reaction from acyl isourea, which is of an active type. Therefore, it is more preferable that the concentration of the matrix is higher, in which case the reaction with the aminoalkyl (meth)acrylate expressed by general formula (5) progresses well to increase the yield.

Specific conditions for the above-described reaction are to be appropriately set in accordance with the concentration of the matrix or the catalyst to be used. General conditions are as follows. The reaction temperature is −20° C. to 150° C., more preferably −10° C. to 100° C., or more preferably 0° C. to 80° C. The reaction time duration is 10 minutes to 72 hours, preferably 30 minutes to 48 hours, or more preferably 1 hour to 24 hours. The pressure may be normal pressure, reduced pressure or increased pressure. The reaction process may be appropriately selected from known processes such as a batch process, a semi-batch process, a continuous process and the like.

For the reactions of production method 1 and production 2 described above, a polymerization inhibitor may be used. Any commonly used polymerization inhibitor may be used with no specific limitation. Examples of the usable polymerization inhibitor include nitroso compounds such as 2,2,6,6-tetramethyl-4-hydroxypiperidine-1-oxyl, N-nitroso phenylhydroxylamine ammonium salt, N-nitroso phenylhydroxylamine aluminum salt, N-nitroso-N-(1-naphtyl)hydroxylamine ammonium salt, N-nitroso diphenylamine, N-nitroso-N-methylaniline, nitrosonaphthol, p-nitorosophenol, N,N'-dimethyl-p-nitrosoaniline and the like;

sulfur-containing compounds such as phenothiazine, methylene blue, 2-mercaptobenzoimidazole, and the like; amines such as N,N'-diphenyl-p-phenylenediamine, N-phenyl-N'-isopropyl-p-phenylenediamine, 4-hydroxydiphenylamine, aminophenol, and the like; quinones such as hydroxyquinoline, hydroquinone, methylhydroquinone, p-benzoquinone, hydroquinone monomethyl ether, and the like; phenols such as p-methoxyphenol, 2,4-dimethyl-6-t-butylphenol, catechol, 3-s-butylcatechol, 2,2-methylenebis-(6-t-butyl-4-methylphenol), and the like; imides such as N-hydroxyphthalimide, and the like; oximes such as cyclohexaneoxime, p-quinonedioxime, and the like; dialkylthiodipropionate; and the like. The polymerization inhibitor is incorporated to have a content of 0.001 to 10 parts by weight, or preferably a content of 0.01 to 1 part by weight, with respect to 100 parts by weight of (meth)acrylic acid, (meth)acrylic acid anhydride or aminoalkyl (meth)acrylate expressed by general formula (5).

In general, the alicyclic ester compound expressed by general formula (1) obtained by any of the above-described production methods is desirably isolated and purified as a desirable high purity monomer by a known separation and purification method such as water-washing, filtration, concentration, distillation, extraction, crystallization, re-crystallization, column chromatography, use of activated carbon or the like, or any combination thereof. Specifically, the reaction solution is washed with water to remove excessive amounts of (meth)acrylic acid, aminoalkyl (meth)acrylate compound, catalyst and other additives. In the case where a water-soluble carbodiimide-based dehydration condensation agent such as 1-ethyl-3-(3-dimethylaminopropyl)carbodiimidehydrochloride or the like is used in the reaction, an excessive amount of the dehydration condensation agent and urea, which is generated by a side reaction, are removed at the same time by water-washing. In this step, the washing water may contain an appropriate inorganic salt such as sodium chloride, sodium hydrogen carbonate, sodium carbonate or the like. The washing may be performed with an aqueous solution of sodium hydroxide, which is alkaline. Since the alicyclic ester compound, used for a resist monomer, needs to be reduced in the amount of metal impurities. Therefore, the metal impurities may be removed by acid washing or use of an ion exchange resin. Usable for the acid washing are, for example, inorganic acid solutions such as an aqueous solution of hydrochloric acid, an aqueous solution of sulfuric acid, an aqueous solution of phosphoric acid, and the like; and organic acid solutions such as an aqueous solution of oxalic acid, and the like. For the washing, the reaction solution may contain an organic solvent or the like. The organic solvent may be the same as, or different from, that used for the reaction. Usually, a solvent that has a low polarity and thus is well separable from water is preferable. The purity may be increased by re-crystallization.

A (meth)acrylic copolymer obtained by copolymerization of the alicyclic ester compound expressed by general formula (1) according to the present invention is usable for a functional resin used for a photoresist. The (meth)acrylic copolymer according to the present invention includes a repeat unit expressed by general formula (6), at least one type of repeat unit selected from general formulae (7) and (8), and at least one type of repeat unit selected from general formulae (9) and (10). The repeat unit of general formula (6) may be obtained by use of the alicyclic ester compound expressed by general formula (1) as a material.

[Chemical formula 23]

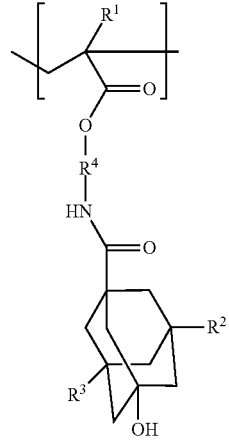

(6)

(In the formula, $R^1$ through $R^4$ are the same as those in general formula (1).)

[Chemical formula 24]

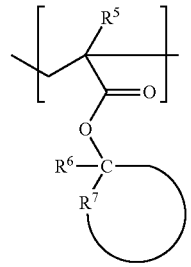

(7)

(In the formula, $R^5$ represents hydrogen or a methyl group, $R^6$ represents an alkyl group having a carbon number of 1 to 4, and $R^7$ represents a cycloalkylene group having a carbon number of 5 to 20, or an alicyclic alkylene group.)

[Chemical formula 25]

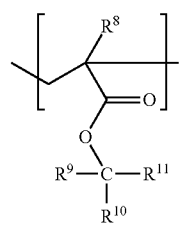

(8)

(In the formula, $R^8$ represents hydrogen or a methyl group, $R^9$ and $R^{10}$ may be the same as, or different from, each other and independently represent an alkyl group having a carbon number of 1 to 4, and $R^{11}$ represents a cycloalkyl group having a carbon number of 5 to 20 or an alicyclic alkyl group which may contain an alkyl group having a carbon number of 1 to 4 or a hydroxyl group.)

[Chemical formula 26]

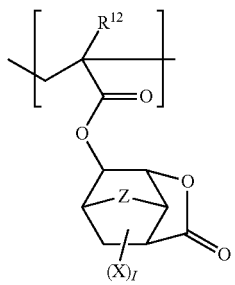

(9)

(In the formula, R$^{12}$ represents hydrogen or a methyl group, Z represents methylene (—CH$_2$—) or oxa(-O—), X(s) may be the same as, or different from, each other and independently represent a hydroxyl group, a halogen group, a nitrile group, a carboxylic acid group, an alkyl carboxylate group having a carbon number of 1 to 4, or an alkoxide group having a carbon number of 1 to 4, and l represents 0 to 2.)

[Chemical formula 27]

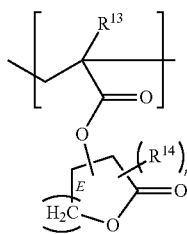

(10)

(In the formula, R$^{13}$ represents hydrogen or a methyl group, m represents 1 to 3, R$^{14}$ represents a methyl group, an ethyl group, a hydroxyl group or a halogen group, and n represents 0 to 2.)

Examples of material of the repeat unit expressed by general formula (7) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethy-2-(meth)acryloyloxydecahydro-1,4:5,8-dimethanonaphthalene, 2-ethyl-2-(meth)acryloyloxynorbornane, and the like.

Examples of material of the repeat unit expressed by general formula (8) include 2-cyclohexyl-2-(meth)acryloyloxypropane, 2-(4-methylcyclohexyl)-2-(meth)acryloyloxypropane, 2,-adamantyl-2-(meth)acryloyloxypropane, 2-(3-(1-hydroxy-1-methylethyl)adamantyl)-2-(meth)acryloyloxypropane, and the like.

Examples of material of the repeat unit expressed by general formula (9) include 2-(meth)acryloyloxy-5-oxo-4-oxatricyclo[4.2.1.0$^{3,7}$]nonane, 7 or 8-(meth)acryloyloxy-3-oxo-4-oxatricyclo[5.2.1.0$^{2,6}$]decane, 9-(meth)acryloyloxy-3-oxo-2-oxa-6-oxa-tricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$]nonane-6-carbonitrile, and the like.

Examples of material of the repeat unit expressed by general formula (10) include α-(meth)acryloyloxy-γ-butyrolactone, β-(meth)acryloyloxy-γ-butyrolactone, (meth)acryloyloxypantolactone, and the like.

The repeat units expressed by general formulae (7) and (8) have a function of being dissociated with an acid. The repeat units expressed by general formulae (7) and (8) have approximately an equal level of performance regarding the dissociation. At least one type of such a repeat unit contained in the (meth)acrylic copolymer reacts with an acid generated from a photoacid generator at the time of exposure to generate a carboxylic acid group and thus the (meth)acrylic copolymer is converted into an alkali-soluble substance.

The repeat units expressed by general formulae (9) and (10) each contain a lactone group. The repeat units expressed by general formulae (9) and (10) have approximately an equal level of performance regarding the lactone group. At least one type of such a repeat unit contained in the (meth)acrylic copolymer improves the solubility in a solvent, the adherence to a substrate, and the affinity to an alkaline developer. Thus, the (meth)acrylic copolymer is usable for photolithography.

In a (meth)acrylic copolymer containing a repeat unit expressed by general formula (6), a repeat unit expressed by general formula (7) or (8), and a repeat unit expressed by general formula (9) or (10), the repeat unit of general formula (6) is contained preferably at a ratio of 5% by weight to 40% by weight with respect to all the repeat units. At least one type of repeat unit of general formula (7) or (8) is contained preferably at a ratio of 20% by weight to 50% by weight with respect to all the repeat units. At least one type of repeat unit of general formula (9) or (10) is contained preferably at a ratio of 15% by weight to 50% by weight with respect to all the repeat units.

The total of the ratios of the repeat unit(s) of general formulae (6) through (8), the repeat unit(s) of general formulae (9) and (10), and the repeat unit(s) of general formulae (11) and (12) is 100% by weight. The (meth)acrylic copolymer according to the present invention may contain any other repeat unit at a ratio of 20% by weight or less, or preferably at a ratio of 10% by weight or less, in addition to the repeat units of general formulae (6) through (12).

Generally for polymerization, the monomer as the repeat unit is dissolved in a solvent, a catalyst is added, and the reaction is caused while the substances are heated or cooled. Conditions of the polymerization reaction may be optionally set in accordance with the type of initiator, the method for initiating polymerization by heat, light, and so on, the temperature, the pressure, the concentration, the solvent, the additives and the like. A polymerization reaction for the (meth)acrylic copolymer according to the present invention may be performed by a known method, for example, radical polymerization using a radical generator such as azoisobutyronitrile, peroxide or the like, or ion polymerization using a catalyst such as alkyllithium, a Grignard reagent or the like.

Examples of the solvent usable for the polymerization reaction for the (meth)acrylic copolymer according to the present invention include ketones such as 2-butanone, 2-heptanone, methyl isobutyl ketone, cyclohexanone and the like; alkanes such as hexane, heptane, octane, cyclohexane, cyclooctane, decalin, norbornane and the like; alcohols such as methanol, ethanol, propanol, 2-propanol, n-butanol, sec-butanol, t-butanol, pentanol, hexanol, propyleneglycol monomethylether, and the like; ethers such as diethylether, tetrahydrofuran, 1,4-dioxane, and the like; and carboxylic acid esters such as ethyl acetate, butyl acetate, methyl lactate, propyleneglycol monomethylether acetate, and the like. These solvents may be used independently or in a combination of two or more thereof.

The (meth)acrylic copolymer obtained by the present invention may be purified by a known method. Specifically, metal impurities may be removed by a combination of any of ultrafiltration, precision filtration, acid washing, water washing with an electric conductivity of 10 mS/m. or less, and extraction. In the case where acid washing is performed, a water-soluble acid may be used, for example, an organic acid such as formic acid, acetic acid, propionic acid or the like, or an inorganic acid such as hydrochloric acid, sulfuric acid, nitric acid, phosphoric acid or the like. In consideration of the separability from the reaction solution, it is preferable to use an inorganic acid. For removing an oligomer, any of ultrafiltration, precision filtration, crystallization, re-crystallization, extraction, water washing with an electric conductivity of 10 mS/m. or less, and the like may be combined.

The (meth)acrylic copolymer according to the present invention has a polystyrene-converted weight-average molecular weight (hereinafter, referred to as "Mw") measured by gel permeation chromatography (GPC) of preferably 1,000 to 500,000, or more preferably 3,000 to 100,000. The ratio of Mw with respect to a polystyrene-converted number-average molecular weight (hereinafter, referred to as "Mn") measured by GPC, namely Mw/Mn, of the (meth) acrylic copolymer is usually 1 to 10, or preferably 1 to 5. According to the present invention, a single type of (meth) acrylic copolymer may be used, or two or more types of (meth)acrylic copolymer may be used in combination.

A photosensitive resin composition according to the present invention may contain the above-described (meth) acrylic copolymer and a photoacid generator that are dissolved in a solvent. Examples of the commonly usable solvent include linear ketones such as 2-pentanone, 2-hexanone and the like; cyclic ketones such as cyclopentanone, cyclohexanone, and the like; propyleneglycol monoalkyl acetates such as propyleneglycol monomethylether acetate, propyleneglycol monoethylether acetate, and the like; ethyleneglycol monoalkylether acetates such as ethyleneglycol monomethylether acetate, ethyleneglycol monoethylether acetate, and the like; propyleneglycol monoalkylethers such as propyleneglycol monomethylether, propyleneglycol monoethylether, and the like; ethyleneglycol monoalkylethers such as ethyleneglycol monomethylether, ethyleneglycol monoethylether, and the like; diethyleneglycol alkylethers such as diethyleneglycol dimethylether, diethyleneglycol diethylether, and the like; esters such as ethyl acetate, ethyl lactate, and the like; alcohols such as cyclohexanol, 1-octanol, and the like; ethylene carbonate; γ-butyrolactone; and the like. These solvents may be used independently or in a combination of two or more thereof.

As the photoacid generator, any substance appropriate for the wavelength of the exposing light may be selected from substances usable as an acid generator for a chemical amplification resist composition, in consideration of the range of thickness of the resist film and the optical absorption coefficient of the substance. A single type of photoacid generator may be used, or two or more types of photoacid generator may be used in combination. The acid generator is contained preferably at 0.1 to 20 parts by weight, or more preferably at 0.5 to 15 parts by weight, with respect to 100 parts by weight of (meth)acrylic copolymer.

Examples of the photoacid generator usable in a far ultraviolet region include onium salt compound, sulfoneimide compound, sulfone compound, sulfonic acid ester compound, quinonediazide compound, diazomethane compound, and the like. Among these photoacid generators, examples of the photoacid generators preferable for a KrF excimer laser, EUV light and an electron beam include onium salt compounds such as sulfonium salt, iodonium salt, phosphonium salt, diazonium salt, pyridinium salt, and the like. Specific examples of such a preferable photoacid generator include triphenylsulfonium trifluoromethanesulfonate, triphenylsulfonium nonafluorobutyrate, triphenylsulfonium hexafluoroantimonate, triphenylsulfonium naphthalenesulfonate, (hydroxyphenyl)benzylmethylsulfonium toluenesulfonate, diphenyliodonium trifluoromethanesulfonate, diphenyliodonium pyrenesulfonate, diphenyliodonium dodecylbenzenesulfonate, diphenyliodonium hexafluoroantimonate, and the like.

An acid diffusion controller may be contained that controls the phenomenon that the acid generated from the acid generator by exposure is diffused in a resist film and thus suppresses a non-preferable chemical reaction in a non-exposed region. A preferable acid diffusion controller is a nitrogen-containing organic compound which does not have a basicity thereof changed by exposure or heating performed during the formation of a resist pattern. Examples of such a nitrogen-containing organic compound include monoalkylamines such as n-hexylamine, n-heptylamine, n-octylamine, and the like; dialkylamines such as di-n-butylamine, and the like; trialkylamines such as trimethylamine, and the like; substituted trialcoholamines such as triethanolamine, tripropanolamine, tributanolamine, tripentanolamine, trihexanolamine, and the like; trialkoxyalkylamines such as trimethoxyethylamine, trimethoxypropylamine, trimethoxybutylamine, triethoxybutylamine, and the like; aromatic amines such as aniline, N,N-dimethylaniline, 2-methylaniline, 3-methylaniline, 4-methylaniline, 4-nitroaniline, diphenylamine, and the like; amine compounds such as ethylenediamine, and the like; amide compounds such as formamide, N,N-dimethylformamide, N,N-dimethylacetamide, N-methylpyrrolidone, and the like; urea compounds such as urea, and the like; imidazoles such as imidazole, benzimidazole, and the like; pyridines such as pyridine, 4-methylpyridine, and the like; 1,4-diazabicyclo[2.2.2]octane; and the like. The acid diffusion controller is contained generally at 15 parts by weight or less, preferably at 0.001 to 10 parts by weight, or more preferably at 0.005 to 5 parts by weight, with respect to 100 parts by weight of (meth)acrylic copolymer.

The photosensitive resin composition according to the present invention may also optionally contain any of various additives used in conventional chemical amplification resist compositions, for example, a surfactant, a quencher, a sensitizer, a halation inhibiting agent, a preservative/stabilizer, a defoamer, and the like.

The photosensitive resin composition according to the present invention is formed into a resist pattern as follows. The composition solution prepared as described above is applied to a substrate formed of, for example, a silicon wafer, a metal material, a plastic material, glass, a ceramic material or the like by use of an appropriate application device such as a spin coater, a dip coater, a roller coater or the like to form a resist film. The resist film is optionally pre-heated at a temperature of about 50° C. to 200° C., and then is exposed to light via a predetermined mask pattern. The resist film has an approximate thickness of, for example, 0.01 to 5 μm, preferably 0.02 to 1 μm, or more preferably 0.02 to 0.1 μm. The exposure may be performed by use of a light beam having any of various wavelengths, for example, ultraviolet light, an X-ray or the like. An appropriate light beam is selected from, for example, far ultraviolet light generated from a light source such as an F2 excimer laser (wavelength: 157 nm), an ArF excimer laser (wavelength: 193 nm) or a KrF excimer laser (wavelength: 248 nm) or the like, EUV light (wavelength: 13 nm), an X-ray, an electronic beam and the like. Exposure conditions including the exposure amount are appropriately selected in accordance with the composition of the photosensitive resin composition, the type of additives and the like.

In the present invention, it is preferable that the heating is performed after the exposure at a temperature of 50 to 200° C. for 30 seconds or longer in order to form a highly precise minute pattern stably. When the temperature is lower than 50° C., there is an undesirable possibility that the sensitivity is largely dispersed in accordance with the type of the substrate. After the heating, development is performed with an alkaline developer usually at 10 to 50° C. for 10 to 200 seconds, or preferably at 20 to 25° C. for 15 to 1200 seconds. In this manner, a predetermined resist pattern is formed.

An example of usable alkaline developer is an alkaline aqueous solution containing an alkaline compound dissolved so as to have a concentration of usually 0.0001 to 10% by weight, preferably 0.01 to 5% by weight, or more preferably 0.1 to 3% by weight. Examples of the alkaline compound include alkali metal hydroxide, ammonia water, alkylamines, alkanolamines, heterocyclic amines, tetraalkylammoniumhydroxides, choline, 1,8-diazabicyclo-[5.4.0]-7-undecene, 1,5-diazabicyclo-[4.3.0]-5-nonene, and the like. The developer containing the alkaline aqueous solution may also optionally contain a water-soluble organic solvent or a surfactant.

The photosensitive resin composition according to the present invention has superb adherence to the substrate and is alkali-soluble, and thus is formed into a minute pattern at high precision.

EXAMPLES

Hereinafter, the present invention will be specifically described by way of examples. The present invention is not limited to any of the following examples. In the examples, the purity and the yield of the novel (meth)acrylic compound were determined by high performance liquid chromatography (HPLC), and the structure thereof was determined by $^1$H and $^{13}$C-NMR. The HPLC measurement conditions were as follows.
<HPLC Measurement Conditions>
Column: L-column ODS L-C18 (5 μm, 4.6φ×250 mm) of Chemicals Evaluation and Research Institute, Japan; developing solvent: acetonitrile/water=40/60 (v/v); flow rate: 1 ml/minute; column temperature: 40° C.; detector: R1

Example 1

Production of 3-hydroxy-N-(2-hydroxyethyl)adamantane-1-carboxamide

[Chemical formula 28]

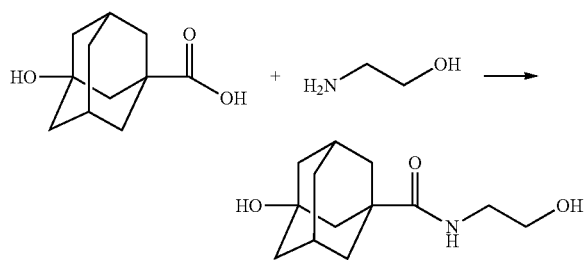

A 100 ml three-necked round bottom flask provided with a stirrer, a thermometer, and a distillation cooling device was supplied with 9.81 g (0.05 mol) of 3-hydroxyadamantane-1-carboxylic acid and 15.27 g (0.25 mol) of ethanolamine, and was heated to 150° C. The temperature was raised from 150° C. to 180° C. over 5 hours. During this time period, generated water was removed by distillation together with ethanolamine. After the reaction was finished, the resultant viscous liquid was dissolved in ethyl acetate, and the resultant solution was provided to fill a silica gel column. A top part of the solution was removed with ethyl acetate, and then the remaining part was fractionated and purified with a developing solvent, which was ethyl acetate/methanol=50/1 (v/v). The solvent was removed by distillation at reduced pressure. As a result, 6.13 g of 3-hydroxy-N-(2-hydroxyethyl)adamantane-1-carboxamide was obtained as a pale orange solid (yield: 51.3%).

$^1$H-NMR spectrum (deuterated DMSO): δ1.5 to 2.1 ppm (14H, adamantane), 3.1 ppm (2H, —NH—CH$_2$—CH$_2$—OH), 3.3 ppm (2H, —NH—CH$_2$—CH$_2$—O—), 4.5 ppm (1H, —NH—CH$_2$—CH$_2$—OH).

$^{13}$C-NMR spectrum (deuterated DMSO): 27.3, 32.4, 35.2, 38.9, 41.8, 44.2 ppm (adamantane), 40.6 ppm (—NH—CH$_2$—CH$_2$—OH), 57.3 ppm (—NH—CH$_2$—CH$_2$—O—), 64.1 ppm (OH-bond of adamantane), 173.7 ppm (carbonyl adamantanecarboxylate group).

Production of 2-(3-hydroxyadamantane-1-carboxamide)ethylmethacrylate

[Chemical formula 29]

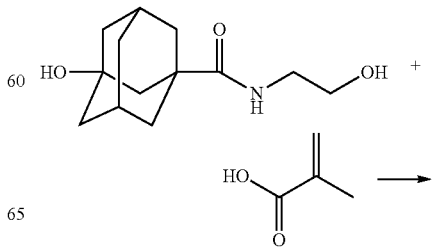

-continued

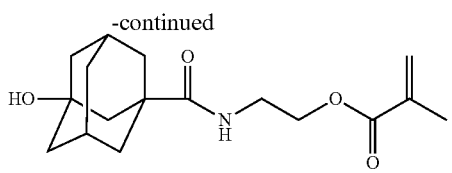

A 200 ml three-necked round bottom flask provided with a stirrer, a thermometer, and a cooling device was supplied with 10.00 g (41.6 mmol) of 3-hydroxy-N-(2-hydroxyethyl) adamantane-1-carboxamide, 1.02 g (8.32 mmol) of 4-dimethylaminopyridine, and 15.95 g (83.2 mmol) of 1-ethyl-3-(3-dimethylaminopropyl)carbodiimidehydrochloride. 7.16 g (83.2 mmol) of methacrylic acid was dissolved in 50 g of 1,2-dichloroethane, and the resultant substance was also supplied to the flask. The reaction solution was heated to 40° C. and stirred for 7 hours. Then, the heating was stopped, the temperature of the solution was lowered to room temperature, and the solution was stirred for 16 hours. After the reaction was finished, 150 ml of ethyl acetate was added, and the resultant solution was transferred to a 500 ml separatory funnel. The organic layer was washed with 100 g of ion exchange water and recovered. The washing water was returned to the separatory funnel, 100 ml of ethyl acetate was added thereto, and the target substance was recovered. The organic layer was also recovered, and 15 mg of p-methoxyphenol was added. The solvent was concentrated in vacuum, and fractionated and purified in a silica gel column (developing solvent: chloroform/methanol=10/1 (v/v); Rf value: 0.35). 10 mg of p-methoxyphenol was added, and the solvent was removed by distillation. As a result, 7.31 g of the target was obtained as a pale yellow solid (yield: 56.7%).

$^1$H-NMR spectrum (CDCl$_3$): δ1.5 to 2.3 ppm (14H, adamantane), 1.9 ppm (3H, methyl group of methacryloyl group), 3.5 ppm (2H, —NH—CH$_2$—CH$_2$—O—), 4.2 ppm (2H, —NH—CH$_2$—CH$_2$—O—), 5.6, 6.1 ppm (2H, double bond of methacryloyl group).

$^{13}$C-NMR spectrum (CDCl$_3$): 15.5 ppm (methyl group of methacryloyl group), 27.2, 32.0, 34.9, 35.9, 41.2, 43.5 ppm (adamantane), 41.0 ppm (—NH—CH$_2$—CH$_2$—O—), 60.3 ppm (OH-bond adamantane), 65.3 ppm (—NH—CH$_2$—CH$_2$—O—), 123.4 ppm (terminus of double bond of methacryloyl group), 132.8 ppm (carbonyl a position of methacryloyl group), 164.7 ppm (methacryloyl group carbonyl group), 173.8 ppm (carbonyl adamantanecarboxylate group).

Example 2

Resin Synthesis Example 1

3.08 g of 2-(3-hydroxyadamantane-1-carboxamide)ethylmethacrylate (hereinafter, referred to as "monomer A1") obtained in Example 1, 4.97 g of 2-ethyl-2-methacryloyloxyadamantane (hereinafter, referred to as "monomer B1"), 3.39 g of α-methacryloyloxy-γ-butyrolactone (hereinafter, referred to as "monomer C1"), and 0.41 g of azobisisobutyronitrile were dissolved in 120 mL of tetrahydrofuran, and polymerization was performed for 15 hours while the reaction temperature was kept at 60° C. in a nitrogen atmosphere (the ratio of monomer amounts was A1/B1/C1=20/40/40 mol %). After the polymerization, the reaction solution was dripped into 600 mL of n-hexane to solidify and purify the resin. The generated white powder was filtrated by a membrane filter and washed with 1000 ml of n-hexane. The white powder was recovered, and dried overnight at 40° C. at reduced pressure. As a result, 8.12 g of methacrylic copolymer P1 was obtained.

Example 3

Resin Synthesis Example 2

3.07 g of 2-(3-hydroxyadamantane-1-carboxamide)ethylmethacrylate (hereinafter, referred to as "monomer A1") obtained in Example 1, 5.25 g of 2-adamantyl-2-methacryloyloxypropane (hereinafter, referred to as "monomer B2"), 4.45 g of 2-methacryloyloxy-5-oxo-4-oxatricyclo[4.2.1.0$^{3,7}$]nonane (hereinafter, referred to as "monomer C2"), and 0.41 g of azobisisobutyronitrile were dissolved in 120 mL of tetrahydrofuran, and polymerization was performed for 15 hours while the reaction temperature was kept at 60° C. in a nitrogen atmosphere (the ratio of monomer amounts was A1/B2/C2=20/40/40 mol %). After the polymerization, the reaction solution was dripped into 600 mL of n-hexane to solidify and purify the resin. The generated white powder was filtrated by a membrane filter and washed with 1000 ml of n-hexane. The white powder was recovered, and dried overnight at 40° C. at reduced pressure. As a result, 7.75 g of methacrylic copolymer P2 was obtained.

Examples 4 and 5

<Resist Performance Evaluation 1>
<Formation of Resist Pattern>

100 parts by weight of each of the obtained methacrylic copolymers and 10 parts by weight of triphenylsulfoniumnonafluorobutanesulfonate (TPS-109 produced by Midori Kagaku Co., Ltd.) were dissolved in ethyl lactate as a solvent such that the copolymer would have a concentration of 6.3% by weight. Thus, a photosensitive resin composition was prepared. A reflection-preventive film (ARC-29 produced by Nissan Chemical Industries, Ltd.) was applied to a silicon wafer, and the prepared resin composition for photoresist was applied to the reflection-preventive film by spin coating to form a photosensitive layer having a thickness of 100 nm. The photosensitive layer was prebaked at a temperature of 90° C. for 60 seconds on a hot plate, and then drawing was performed by an electron beam drawing device (ELS-7700 produced by Elionix Inc.) The resultant layer was post-baked (PEB) for 90 seconds at a temperature optimized for the corresponding resin composition for photoresist, and then was developed for 60 seconds with an aqueous solution of 0.3 M of tetramethylammoniumhydroxide and rinsed with pure water to obtain a line-and-space pattern.

The created line-and-space pattern was observed by an FE-SEM, and the exposure amount at which an image of 1:1 line-and-space pattern of 100 nm was resolved was set as the optimal exposure amount Eop (μC/cm$^2$). In addition, the roughness of the pattern (line edge roughness: LER) was measured. The results are shown in Table 1.

TABLE 1

| Photosensitive Resin Composition | Copolymer | Copolymerizable monomer | PEB temperature °C. | Optimal Exposure Amount μC/cm² | LER nm |
|---|---|---|---|---|---|
| Example 4 | R1 | P1 | A1/B1/C1 | 110 | 58 | 9.2 |
| Example 5 | R2 | P2 | A2/B2/C2 | 140 | 70 | 13.4 |

From the results shown in Table 1, R1 and R2 as the photosensitive resin compositions in Examples 4 and 5 were confirmed to have superb characteristics. Specifically, with the photosensitive resin compositions in both of examples, the roughness of the pattern (LER) was suppressed with no need of a high PEB temperature or the optimal exposure amount.

The invention claimed is:

1. A method for producing an alicyclic ester compound expressed by general formula (1):

[Chemical formula 1]

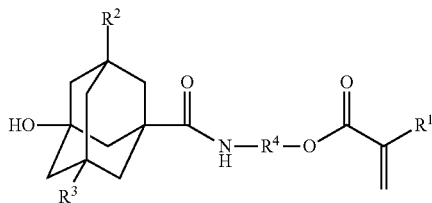

(1)

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5;

the method comprising reacting an adamantane compound expressed by general formula (2) with hydroxyalkylamine expressed by general formula (3) to produce an adamantaneamide compound expressed by general formula (4), and then reacting the adamantaneamide compound expressed by general formula (4) with (meth)acrylic acid:

[Chemical formula 2]

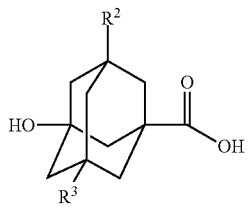

(2)

where $R^2$ and $R^3$ are the same as those in chemical formula (1);

[Chemical formula 3]

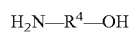

(3)

where $R^4$ is the same as that in chemical formula (1);

[Chemical formula 4]

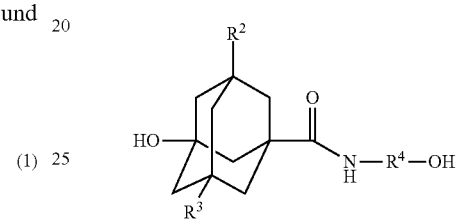

(4)

where $R^2$, $R^3$ and $R^4$ are the same as those in chemical formula (1).

2. The method for producing an alicyclic ester compound according to claim 1, the method comprising the step of heating the adamantane compound expressed by general formula (2) and the hydroxyalkylamine expressed by general formula (3) to cause dehydration condensation to produce the adamantaneamide compound expressed by general formula (4) as shown below:

[Chemical formula 5]

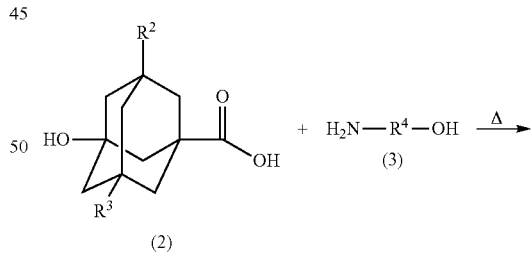

(2)                (3)

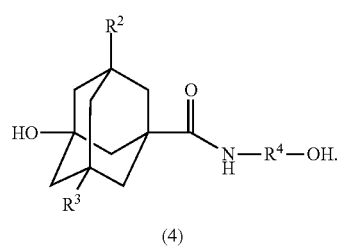

(4)

3. A method for producing an alicyclic ester compound expressed by general formula (1):

[Chemical formula 6]

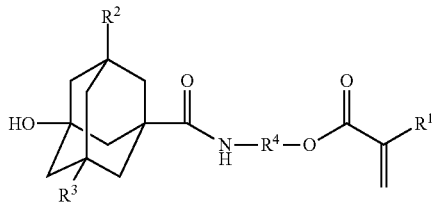

(1)

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5;

the method comprising reacting an adamantane compound expressed by general formula (2) with aminoalkyl (meth)acrylate expressed by general formula (5) to produce the alicyclic ester compound expressed by general formula (1):

[Chemical formula 7]

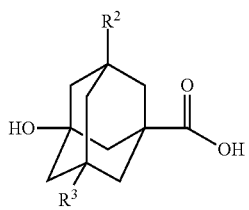

(2)

where $R^2$ and $R^3$ are the same as those in chemical formula (1);

[Chemical formula 8]

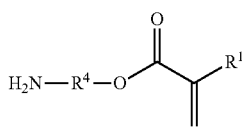

(5)

where $R^1$ and $R^4$ are the same as those in chemical formula (1).

4. The method for producing an alicyclic ester compound according to claim 3, wherein the reaction, expressed by the following formula, of the adamantane compound expressed by general formula (2) and the aminoalkyl (meth)acrylate expressed by general formula (5) uses a dehydration condensation agent:

[Chemical formula 9]

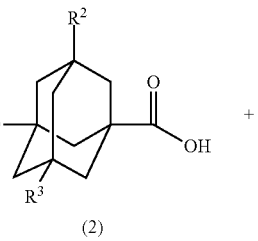

(2)

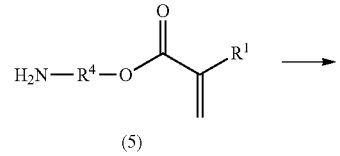

(5)

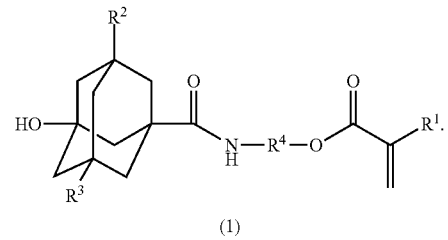

(1)

5. A (meth)acrylic copolymer, comprising a repeat unit expressed by general formula (6), the (meth)acrylic copolymer being obtained by polymerization of the alicyclic ester compound produced by the method according to claim 1:

[Chemical formula 10]

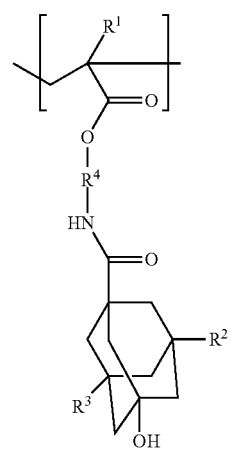

(6)

where $R^1$ through $R^4$ are the same as those in general formula (1).

6. The (meth)acrylic copolymer according to claim 5, further comprising at least one type of repeat unit expressed by general formula (7) or (8) and at least one type of repeat unit expressed by general formula (9) or (10):

[Chemical formula 11]

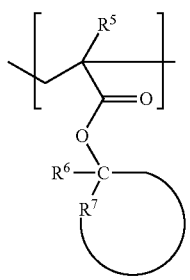

(7)

where $R^5$ represents hydrogen or a methyl group, $R^6$ represents an alkyl group having a carbon number of 1 to 4, and $R^7$ represents a cycloalkylene group having a carbon number of 5 to 20, or an alicyclic alkylene group;

[Chemical formula 12]

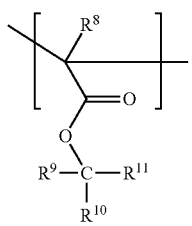

(8)

where $R^8$ represents hydrogen or a methyl group, $R^9$ and $R^{10}$ may be the same as, or different from, each other and independently represent an alkyl group having a carbon number of 1 to 4, and $R^{11}$ represents an alkyl group having a carbon number of 1 to 4, a cycloalkyl group having a carbon number of 5 to 20, or an alicyclic alkyl group;

[Chemical formula 13]

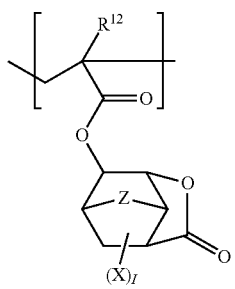

(9)

where $R^{12}$ represents hydrogen or a methyl group, Z represents methylene(-$CH_2$—) or oxa(-O—), X(s) may be the same as, or different from, each other and independently represent a hydroxyl group, a halogen group, a nitrile group, a carboxylic acid group, an alkyl carboxylate group having a carbon number of 1 to 4, or an alkoxide group having a carbon number of 1 to 4, and l represents 0 to 2;

[Chemical formula 14]

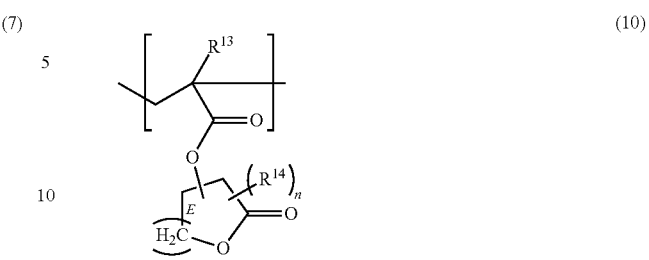

(10)

where $R^{13}$ represents hydrogen or a methyl group, m represents 1 to 3, $R^{14}$ represents a methyl group, an ethyl group, a hydroxyl group or a halogen group, and n represents 0 to 2.

7. A photosensitive resin composition, comprising the (meth)acrylic copolymer according to claim 5 and a photoacid generator.

8. An alicyclic ester compound expressed by general formula (1):

[Chemical formula 15]

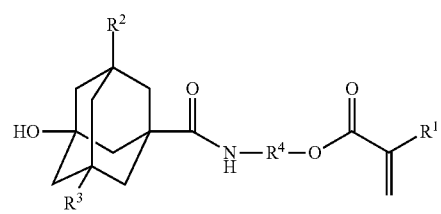

(1)

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5.

9. A (meth)acrylic copolymer, comprising a repeat unit expressed by general formula (6), the (meth)acrylic copolymer being obtained by polymerization of the alicyclic ester compound produced by the method according to claim 3:

[Chemical formula 10]

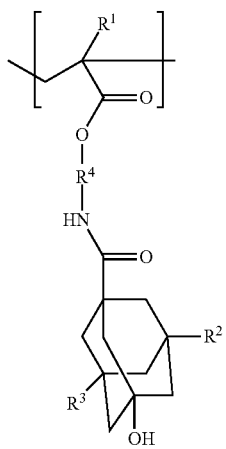

(6)

where $R^1$ through $R^4$ are the same as those in general formula (1).

10. The (meth)acrylic copolymer according to claim 9, further comprising at least one type of repeat unit expressed by general formula (7) or (8) and at least one type of repeat unit expressed by general formula (9) or (10):

[Chemical formula 11]

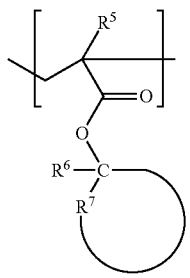

(7)

where $R^5$ represents hydrogen or a methyl group, $R^6$ represents an alkyl group having a carbon number of 1 to 4, and $R^7$ represents a cycloalkylene group having a carbon number of 5 to 20, or an alicyclic alkylene group;

[Chemical formula 12]

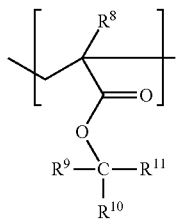

(8)

where $R^8$ represents hydrogen or a methyl group, $R^9$ and $R^{10}$ may be the same as, or different from, each other and independently represent an alkyl group having a carbon number of 1 to 4, and $R^{11}$ represents an alkyl group having a carbon number of 1 to 4, a cycloalkyl group having a carbon number of 5 to 20, or an alicyclic alkyl group;

[Chemical formula 13]

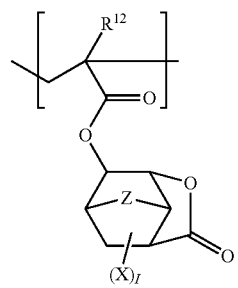

(9)

where $R^{12}$ represents hydrogen or a methyl group, Z represents methylene($-CH_2-$) or oxa($-O-$), X(s) may be the same as, or different from, each other and independently represent a hydroxyl group, a halogen group, a nitrile group, a carboxylic acid group, an alkyl carboxylate group having a carbon number of 1 to 4, or an alkoxide group having a carbon number of 1 to 4, and I represents 0 to 2;

[Chemical formula 14]

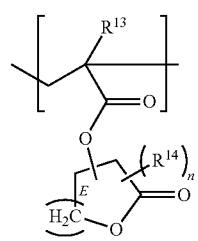

(10)

where $R^{13}$ represents hydrogen or a methyl group, m represents 1 to 3, $R^{14}$ represents a methyl group, an ethyl group, a hydroxyl group or a halogen group, and n represents 0 to 2.

11. A photosensitive resin composition, comprising the (meth)acrylic copolymer according to claim 6 and a photoacid generator.

12. The (meth)acrylic copolymer according to claim 6, wherein the copolymer comprises the repeat unit expressed by general formula (6) at a ratio of 5% by weight to 40% by weight, the repeat unit expressed by general formula (7) or (8) at a ratio of 20% by weight to 50% by weight, and the repeat unit expressed by general formula (9) or (10) at a ratio of 15% by weight to 50%, with respect to all the repeat units.

13. The (meth)acrylic copolymer according to claim 10, wherein the copolymer comprises the repeat unit expressed by general formula (6) at a ratio of 5% by weight to 40% by weight, the repeat unit expressed by general formula (7) or (8) at a ratio of 20% by weight to 50% by weight, and the repeat unit expressed by general formula (9) or (10) at a ratio of 15% by weight to 50%, with respect to all the repeat units.

* * * * *